United States Patent

Beller et al.

(10) Patent No.: US 8,440,167 B2
(45) Date of Patent: May 14, 2013

(54) MULTIMODAL IMAGING OF ATHEROSCLEROTIC PLAQUE TARGETED TO LOX-1

(75) Inventors: George A. Beller, Charlottesville, VA (US); David K. Glover, Charlottesville, VA (US); Alexander L. Klibanov, Charlottesville, VA (US); Craig H. Meyer, Charlottesville, VA (US); Dayuan Li, Charlottesville, VA (US); Amit Patel, Chicago, IL (US); Christopher M. Kramer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 107 days.

(21) Appl. No.: 13/126,029

(22) PCT Filed: Oct. 26, 2009

(86) PCT No.: PCT/US2009/062063
§ 371 (c)(1),
(2), (4) Date: Apr. 26, 2011

(87) PCT Pub. No.: WO2010/062557
PCT Pub. Date: Jun. 3, 2010

(65) Prior Publication Data
US 2011/0223103 A1 Sep. 15, 2011

Related U.S. Application Data (60) Provisional application No. 61/108,701, filed on Oct. 27, 2008, provisional application No. 61/221,331, filed on Jun. 29, 2009.

(51) Int. Cl.
*A61K 49/16* (2006.01)
*A61K 51/10* (2006.01)
*A61K 51/12* (2006.01)
*A61K 39/395* (2006.01)
*A61B 5/055* (2006.01)
*C07K 16/00* (2006.01)

(52) U.S. Cl.
USPC ..... 424/1.37; 424/1.49; 424/1.53; 424/9.321; 424/143.1

(58) Field of Classification Search ...................... None
See application file for complete search history.

(56) References Cited

U.S. PATENT DOCUMENTS

| 5,652,516 | A  | * | 7/1997 | Adalsteinsson et al. | ....... 324/309 |
| 8,108,024 | B2 | * | 1/2012 | Carlsen et al. | ................. 600/407 |
| 2005/0089470 | A1 | | 4/2005 | Johnson et al. | |
| 2005/0089471 | A1 | * | 4/2005 | Johnson et al. | .............. 424/1.11 |
| 2006/0034761 | A1 | | 2/2006 | Syud et al. | |
| 2006/0073100 | A1 | | 4/2006 | Fischman et al. | |
| 2007/0010577 | A1 | * | 1/2007 | Lanza et al. | .................. 514/475 |
| 2008/0019907 | A1 | | 1/2008 | Klaveness et al. | |
| 2008/0118439 | A1 | | 5/2008 | Hancu et al. | |
| 2008/0193376 | A1 | | 8/2008 | Tawakol et al. | |

OTHER PUBLICATIONS

Ishino, S., et al., "Targeting of Lectinlike Oxidized Low-Density Lipoprotein Receptor 1 (LOX-1) with 99mTc-Labeled Anti-LOX-1 Antibody: Potential Agent for Imaging of Vulnerable Plaque", J. Nucl. Med., 2008 (Epub. Sep. 15, 2008), vol. 49, No. 10, pp. 1677-1685.
Li, Dayuan, et al., "Molecular Imaging of Atherosclerotic Plaques Targeted to Oxidized LDL Receptor LOX-1 by SPECT/CT and Magnetic Resonance", Circ. Cardiovasc. Imaging, Jul. 2010, pp. 464-472.
Carrion, C., et al., "Preparation of long-circulating immunoliposomes using PEG-cholesterol conjugates: effect of the spacer arm between PEG and cholesterol on liposomal characteristics", Chemistry and Physics of Lipids, 113 (2001), 97-110.
Hag, Anne Mette Fisker, et al., "Gene expression of LOX-1, VCAM-1, and ICAM-1 in pre-atherosclerotic mice", Biochem. Blophys. Res. Commun. (2008), doi: 10.1016/j.bbrc.2008.10.037, pp. 1-5.
Huwyler, Jörg, et al., "Receptor Mediated Delivery of Daunomycin Using Immunoliposomes: Pharmacokinhetics and Tissue Disgribution in the Rat1", JPET 282: 1541-1546, 1997.
Nakamura, M., et al., "Generation of monoclonal antibodies against a soluble form of lectin-like oxidized low-density lipoprotein receptor-1 and development of a sensitive chemiluminescent enzyme immunoassay", Journal of Pharmaceutical and Biomedical Analysis 51 (2010), 158-163.
Li, D., et al., "Abstract 5791: Detection and Assessment of Atherosclerotic Plaques Using a Radiolabeled Molecular Imaging Probe Targeted to the Oxidized Low Density Lipoprotein Receptor LOX-1", Circulation, 2008: 118:S_103.
Li, D., et al., "Molecular imaging of atherosclerotic plaque targeted to oxidized LDL receptor LOX-1 using magnetic resonance", Jrnl. of Cardiovascular Magnetic Resonance, 2009, 11 (Supp) 1:) 076.

* cited by examiner

*Primary Examiner* — Phuong Huynh
(74) *Attorney, Agent, or Firm* — Rodney L. Sparks (57) ABSTRACT The present invention provides multiple modalities for detecting LOX-1. More particularly, an imaging composition is provided that allows for the in vivo imaging of atherosclerotic plaque.

2 Claims, 5 Drawing Sheets

Atherosclerotic plaque

Fig. 4A

LOX-1

MULTIMODAL IMAGING OF ATHEROSCLEROTIC PLAQUE TARGETED TO LOX-1

CROSS-REFERENCE TO RELATED APPLICATIONS

This application is a national stage filing of International Application No. PCT/US2009/062063, filed Oct. 26, 2009, which claims priority under 35 USC §119(e) to U.S. Provisional Application Ser. Nos. 61/108,701, filed Oct. 27, 2008 and 61/221,331, filed Jun. 29, 2009, the disclosures of which are incorporated herein by reference in their entirety.

BACKGROUND

Cardiovascular disease (CVD) is the leading cause of mortality and morbidity in the United States. One third of adult men and women have some form of CVD. The estimated direct and indirect cost of CVD for 2006 is $403 billion. Atherosclerosis is a major cause of severe cardiovascular diseases including myocardial ischemia, acute myocardial infarction and stroke. There are currently no clinically established non-invasive methods for staging atherosclerotic lesions and detecting vulnerable atherosclerotic plaque. As disclosed herein, novel non-invasive imaging methods targeted at a specific marker of vulnerable and advanced atherosclerotic plaque are provided. These noninvasive molecular imaging techniques can be used to assess plaque complication risk and myocardial ischemia.

Molecular tools are rapidly elucidating the molecular and cellular processes underlying atherosclerosis, myocardial ischemia and infarction. To further understand these biological processes in vivo, investigators are embracing the burgeoning field of molecular imaging. Recent technological developments including cardiac MRI, CT angiography, echocardiography with contrast agents and hybrid PET/CT and SPECT/CT scanners have extended imaging capabilities from the assessment of myocardial perfusion and function alone to permit more detailed characterization of plaques, such as advanced and vulnerable plaques and the degree of plaque remodeling.

It is widely appreciated that the oxidized form of low density lipoprotein (ox-LDL) is more important than native LDL in atherogenesis. Ox-LDL causes expression of adhesion molecules and free radical generation, injures endothelial cells, decreases constitutive nitric oxide synthase (cNOS) activity, and facilitates monocyte/macrophage adhesion on the activated endothelium. Many studies have demonstrated that these effects of ox-LDL are mediated by the interaction of ox-LDL with its receptor LOX-1.

LOX-1 is a classic type II transmembrane protein with a short intracellular cytoplasmic tail and a long extracellular domain containing a C-type lectin-like structure. LOX-1 expression is stimulated by shear stress, cytokines, angiotensin II (Ang II) and ischemia-reperfusion in endothelial cells, smooth muscle cells and macrophages. LOX-1 expression is markedly increased in atherosclerotic plaques in different animal models. Importantly, recent studies have demonstrated that LOX-1 deficiency significantly decreases the formation of atherosclerotic lesions.

SUMMARY OF THE INVENTION

The present invention encompasses multimodality targeted imaging using LOX-1 as target. In one embodiment, a liposome can be used as a linker molecule between a LOX-1 specific binding reagent and one or more detectable markers selected from MRI, PET and SPECT related markers. In one aspect, when MRI is used for the in vivo detection of LOX-1, a novel pulse sequence is provided. In one aspect, the LOX-1 specific binding agent is an antibody, and in a further embodiment the antibody directed against LOX-1 is an antibody fragment.

Applicants studies have shown that the amino acid segment from 162-168 in the extracellular domain of the LOX-1 is responsible for binding Ox-LDL. Based on the results disclosed herein and what is known in the art, without wishing to be bound by any particular theory, applicants believe that there is a significant opportunity to use non-invasive molecular imaging techniques targeting LOX-1 to stage atherosclerotic lesions and to detect vulnerable plaque. Three specific molecular probes have been designed and tested: a gadolinium-LOX-1 antibody-fluorescence probe, a microbubble-LOX-1 antibody-fluorescence probe and an $^{111}$Indium-LOX-1 antibody probe.

In accordance with one embodiment a non-invasive method of in vivo imaging of atherosclerotic plaques in a mammalian species is provided. The method comprises the steps of administering a LOX-1 imaging composition to the patient, waiting for a sufficient amount of time to allow the imaging component to bind to LOX-1 sites in vivo and then imaging the relevant tissues (e.g. the vascular system). Typically the LOX-1 imaging composition is administered by injection parenterally, and more particularly the composition is administered by intravenous injection. In one embodiment the LOX-1 imaging composition comprises a plurality of liposome carriers having a mean diameter of less than 100 nm and a pharmaceutically acceptable carrier. Each of the liposomes is formed from one or more lipids selected from the group consisting of 1,2-Dioleoyl-sn-Glycero-3-Phosphocholine, cholesterol, distearoylphosphatidylethanolamine, N-hydroxysuccinimide ester of carboxy-PEG-DSPE, and at least one additional polymer selected from the group consisting of 1,1'dioctadecyl-3,3,3',3'-tetramethylindocarbocyanine perchlorate, diethylenetriaminepentaacetic acid α,ω-bis(8-stearoylamido-3,6-diaoxaoctylamide)gadolinium complex and DTPA-phosphatidylethanolamine-SPECT contrast agent. In one embodiment the SPECT contrast agent is Tc99m that is covalently bound to isolink or HYNIC. The LOX-1 antibody can be linked to any of the lipids comprising the liposome using standard techniques, and in one embodiment the antibody is linked to the lipid N-hydroxysuccinimide ester of carboxy-PEG-DSPE (e.g. N-hydroxysuccinimide ester of carboxy-PEG-DSPE-LOX-1 antibody).

BRIEF DESCRIPTION OF THE DRAWINGS

FIGS. 2A-2C FIG. 2A is a graph of experimental data showing that LOX-1 probe ($^{111}$In-liposome-LOX-1 Antibody-DiI) bound to LOX-1 antigen in vitro.

FIGS. 5A & 5B are bar graph depictions of the data produced by MR imaging data. Post-injection gadolinium enhancement was found in aortic root to arch in the LDLR−/− mice injected with LOX-1 probes (D, n=7) compared to pre-injection imaging. These findings were confirmed by ex vivo fluorescence imaging of frozen sections that showed LOX-1 probe binding in the same area of atherosclerotic plaque.

The summarized MRI data showed that LDLR−/− mice injected with LOX-1 probe increased contrast to noise ratio (CNR; FIG. 5A) and normalized enhancement ratio (NER; FIG. 5B) compared with other two control groups. Group I=LOX-1 probe injected into LDLR−/− mice; Group II=nIgG probe injected into LDLR−/− mice; Group III=LOX-1 probe injected into LDLR/LOX-1−/− mice.

DETAILED DESCRIPTION

Abbreviations

LDL: low density lipoprotein.
ox-LDL: oxidized form of low density lipoprotein.
LDLR: the LDL receptor.
cNOS: constitutive nitric oxide synthase.
LOX-1: receptor for ox-LDL.
LDLR−/− mice: mice with a double deletion of the LDL receptor.
CNR: contrast to noise ratio.
NER: normalized enhancement ratio.
MRI: Magnetic Resonance Imaging.
CT: Computed Tomography.
SPECT: Single Photon Emission Computed Tomography.
PET: Positron Emission Tomography.
CMR: Cardiovascular Magnetic Resonance.
PEG-DSPE: polyethylene glycol-distearoylphosphatidylethanolamine.
MMPs: Matrix Metalloproteinases.
DiI: 1,1′dioctadecyl-3,3,3′,3′-tetramethylindocarbocyanine perchlorate.
HYNIC: hydrazinonicotinamide.

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 10%.

The term "statins" (or HMG-CoA reductase inhibitors) is intended to encompass the class of drugs known to lower cholesterol levels in people. Typically, statins function by inhibiting the activity of the enzyme HMG-CoA reductase.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

The term, "parenteral" means not through the alimentary canal but by some other route such as subcutaneous, intramuscular, intraspinal, or intravenous.

As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 7. Absent any further characterization, the term is intended to include polymers of ethylene glycol with an average total molecular weight selected from the range of 500 to 40,000 Daltons. "Polyethylene glycol chain" or "PEG chain" is used in combination with a numeric suffix to indicate the approximate average molecular weight thereof. For example, PEG-3400 refers to polyethylene glycol chain having a total molecular weight average of about 3,400.

As used herein a "linker" is a bond, a molecule, or group of molecules that binds two separate entities to one another. The term "linked" refers to compounds that are connected via a linker. The linkage may be either via one or more covalent or non-covalent bonds.

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (mAb) is meant to include intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl, et al., J Nucl Med 24:316 (1983)).

"Liposome" refers to a generally spherical or spheroidal cluster or aggregate of amphipathic compounds, including lipid compounds, typically in the form of one or more concentric layers, for example, monolayers or bilayers containing an entrapped aqueous volume. The liposomes may be formulated, for example, from ionic lipids and/or non-ionic lipids. Micelles are spherical colloidal nanoparticles into which many amphiphilic molecules self-assemble. The term "lipid vesicles" is intended to encompass both micelles and liposomes.

The term "label" or "detectable marker" as used herein refers to any atom or molecule which can be used to provide a detectable (preferably quantifiable) "signal", and which can be linked to another moiety. Labels may provide "signals" detectable by fluorescence, density, radioactivity, colorimetry, gravimetry, X-ray diffraction or absorption, magnetism, enzymatic activity, and the like.

EMBODIMENTS

Many studies have demonstrated that oxidized low density lipoprotein (ox-LDL) plays a critical role in atherogenesis. The ox-LDL receptor LOX-1 mediates the pathological effects of ox-LDL in atherosclerotic lesions. LOX-1 is a type II transmembrane protein with a short intracellular cytoplasmic tail and a long extracellular domain containing a C-type lectin-like structure. LOX-1 induces free radical generation, apoptosis of endothelial cells and monocytes/macrophages, expression of adhesion molecules and activates the inflammatory cascade. LOX-1 also induces expression and activation of matrix metalloproteinases (MMPs). These pathological effects of LOX-1 not only initiate atherosclerotic lesion formation, but also contribute to the vulnerability of a plaque to rupture. A recent study (Mehta et al., Circulation Research, 2007; 100:1634-1642) demonstrated that LOX-1 deficiency significantly decreases the formation of atherosclerotic lesions. In addition, LOX-1 is highly expressed in advanced atherosclerotic plaque and activated endothelial cells, macrophages, platelets and dendritic cells. Besides being highly expressed, its activation leads to apoptosis, free radical generation, inflammatory cell recruitment, and expression of MMPs and tissue factor. Therefore, one advantage of using LOX-1 as a molecular imaging target relative to other markers associated with atherosclerotic plaque is that LOX-1 may represent the full spectrum of pathological processes in atherosclerotic plaque.

As disclosed herein a novel non-invasive imaging probe targeted to LOX-1 is provided. In accordance with one embodiment the imaging probe comprises a LOX-1 specific binding reagent linked to a detectable marker. In one embodiment the detectable marker is a marker that can be safely administered to a living mammalian species and is detectable in vivo. Typically the LOX-1 imaging composition is administered by injection parenterally, and more particularly the composition is administered by intravenous injection. In accordance with one embodiment the detectable marker is a radionuclide or a MRI contrast agent. In one embodiment the marker is a radionuclide, including for example, one selected from the group consisting of $^{99m}$Tc, $^{111}$In, and $^{123}$I and the marker is detected in vivo by Single Photon Emission Computed Tomography (SPECT). In another embodiment the marker is a radionuclide, including for example, one selected from the group consisting of $^{18}$F and $^{64}$Cu and the marker is detected in vivo by Positron Emission Tomography (PET). In another embodiment the marker is a magnetic resonance imaging agent and the marker is detected in vivo by MRI. In one embodiment the magnetic resonance imaging agent, is selected from the group consisting of Gadolinium-based contrast agents, such as Gd-DTPA and related agents; 19 Fluorine-based agents, such as perfluorocarbons, including perfluoro-15-crown-5 ether; and iron oxide particles, including superparamagnetic iron oxide (SPIO) and ultrasmall superparamagnetic iron oxide (USPIO) particles, as well as any combinations of such radionuclide or a MRI contrast agent. In accordance with one embodiment it is advantageous to include both Gadolinium and 19F in the same contrast agent, thereby increasing the signal from 19F (by reducing its T1 relaxation time). In accordance with one embodiment it is advantageous to include both a PET imaging agent and a magnetic resonance imaging agent on the same imaging probe targeted to LOX-1.

In accordance with one embodiment a LOX-1 imaging composition is provided comprising a LOX-1 imaging reagent and a pharmaceutically acceptable carrier. In one embodiment the LOX-1 imaging reagent comprises a liposome or micelle as a linker for the LOX-1 targeting agent and the in vivo detectable marker. In one embodiment the liposomes or micelles are selected to have a mean diameter of less than 100 nm. In one embodiment the mean diameter of the liposomes/micelles is selected from the range of 1 to 90, 10 to 90, 10 to 80, 10 to 70, 20 to 60, 30 to 70, 30 to 80, 40 to 90, 40 to 80, 50 to 80, 50 to 90 or 60 to 90 nm.

The LOX-1 targeting agent can be linked to the liposome or micelle using standard techniques known to those skilled in the art. For example in one embodiment, either before or after formation of the liposome or micelle, reactive groups on the component lipids comprising the liposome are activated and LOX-1 targeting agent and detectable markers are covalently linked to the lipids in a manner that the linked components extend away from the exterior surface of the liposome/micelle. In an alternative embodiment the detectable marker could also be entrapped within the liposome.

In one embodiment the LOX-1 targeting agent is an antibody that specifically binds to the extracellular domains of the LOX-1. In accordance with one embodiment the antibody is a monoclonal antibody. In one embodiment the antibody is linked to the exterior surface of the liposome/micelle by covalent coupling between the antibody protein amino group and an activated carboxyl of a PEG-lipid component of the liposome/micelle.

In accordance with one embodiment the LOX-1 targeting agent is a liposome having a diameter of less than 100 nm and decorated with the respective LOX__1 targeting agent and one or more detectable markers. Liposomes according to the invention may be produced from combinations of lipid materials well known and routinely utilized in the art to produce liposomes. Lipids may include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcho lines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcho lines including, but not limited to, distearoylphosphatidylcho line (DSPC), distearoylphosphatidylethanolamine (DSPE), hydrogenated soy phosphatidylcho line (HSPC), soy phosphatidylcho line (soy PC), egg phosphatidylcho line (egg PC), hydrogenated egg phosphatidylcho line (HEPC), dipalmitoylphosphatidylcho line (DPPC) and dimyristoylphosphatidylcho line (DMPC) are suitable phosphatidylcho lines for use in this invention. All of these phospholipids are commercially available. Further, phosphatidylglycerols (PG) and phosphatic acid (PA) are also suitable phospho lipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Other suitable phospho lipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. Preferred lipids for producing liposomes according to the invention include 1,2-Dioleoyl-sn-Glycero-3-Phosphocho line, cholesterol, and distearoylphosphatidylethanolamine.

Further, incorporation of polyethylene glycol (PEG) containing phospholipids (such as PEG-DSPE) is also contemplated by the present invention. In accordance with one embodiment the liposome comprises an N-hydroxysuccinimide ester of carboxy-PEG-DSPE that is linked to a LOX-1 antibody via the antibody protein amino group and an activated carboxyl of PEG-DSPE. The liposome of the LOX-1 targeting agent further comprises at least one additional polymer selected from the group consisting of a lipid linked fluorescent agent, a lipid linked MR contrast agent and a lipid linked SPECT agent. In one embodiment the fluorescent agent is 1,1'dioctadecyl-3,3,3',3'-tetramethylindocarbocyanine perchlorate (DiI), the lipid linked MR contrast agent is 1,1'dioctadecyl-3,3,3',3'-tetramethylindocarbocyanine perchlorate, diethylenetriaminepentaacetic acid α,ω-bis(8-stearoylamido-3,6-diaoxaoctylamide)gadolinium complex, and the lipid linked SPECT contrast agent is DTPA-phosphatidylethanolamine-$^{111}$In.

In accordance with one embodiment the LOX-1 targeting liposome comprises 1,2-Dioleoyl-sn-Glycero-3-Phosphocholine, cholesterol, N-hydroxysuccinimide ester of carboxy-PEG3400-DSPE linked to a LOX-1 antibody, 1,1'dioctadecyl-3,3,3',3'-tetramethylindocarbocyanine perchlorate, and either a diethylenetriaminepentaacetic acid α,ω-bis(8-stearoylamido-3,6-diaoxaoctylamide)gadolinium complex or DTPA-phosphatidylethanolamine linked to a SPECT contrast agent, or two or more compounds selected form the group consisting of 1,1'dioctadecyl-3,3,3',3'-tetramethylindocarbocyanine perchlorate, diethylenetriaminepentaacetic acid α,ω-bis(8-stearoylamido-3,6-diaoxaoctylamide)gadolinium complex and DTPA-phosphatidylethanolamine linked to a SPECT contrast agent. In one embodiment the SPECT contrast agent is selected from the group consisting of $^{99m}$Tc, $^{111}$In, and $^{123}$I, and in a further embodiment the SPECT contrast agent is $^{111}$In, or $^{123}$I. In one embodiment the magnetic resonance imaging agent, is perfluoro-15-crown-5 ether.

In accordance with one embodiment a liposome consisting of 1,2-Dioleoyl-sn-Glycero-3-Phosphocholine (Avanti Lipids, Alabaster, Ala.), cholesterol (Sigma), N-hydroxysuccinimide ester of carboxy-PEG3400-DSPE (Shearwater Polymers) and DiI (Invitrogen) at a mass ratio of 50:25:25:1 is provided. If liposomes were used to make imaging probes for MRI, diethylenetriaminepentaacetic acid α,ω-bis(8-stearoylamido-3,6-diaoxaoctylamide)gadolinium complex (Sigma) or other suitable MR imaging agent linked to a lipid was added as 1:1 mass ratio with phosphatidylcholine. Lipids were completely dissolved in chloroform and subjected to rotary evaporation in a glass vial under vacuum to create a thin uniform layer of dry lipid on the glass surface. Citrate buffer (10 mM, pH 4.4) was quickly added, mixture agitated to prepare multilamellar liposomes, and then rapidly passed through a 100 nm filter 40 times using a Liposofast device (Avestin). Liposomes (~100 nm in size) were immediately mixed with LOX-1 or nonspecific IgG antibody (R&D Systems, 250 μg in 10 mM HEPES buffer, pH 8.0) overnight at 4° C., so that covalent coupling between the protein amino group and activated carboxyl of PEG-lipid would occur. The compounds were subjected to repeated ultracentrifugation to remove free antibodies. Finally the immunoliposome pellets (probes) were dispersed in PBS buffer.

For $^{111}$In labeling, liposomes carried a trace amount of DTPA-phosphatidylethanolamine. The liposome preparations were mixed with $^{111}$In (Perkin Elmer Life Sciences) in acetate acid buffer (0.5 M, pH 6.0) for 2 hrs at room temperature and then filtrated by a single passage through a Sephadex G50 gel column with a centrifuge at 1000 g for 1 min. The imaging probe consisted of liposomes decorated with anti-LOX-1 antibody (called LOX-1 probe) or non-specific nIgG (called nIgG probe), $^{111}$Indium for SPECT (or Gadolinium for MR imaging) and DiI fluorescence markers.

Compositions comprising a mixture of $^{111}$In labeled liposomes and Gadolinium labeled liposomes can be prepared. Alternatively, individual liposomes can be prepared that contain both radionuclide linked lipids and gadolinium linked lipids. Administration of such mixtures or dual labeled liposome can be used to allow for dual modality scanning or to allow sequential scanning to be conducted using MRI, PET or SPECT analysis. Techniques and reagents useful for the present invention, include, but are not limited to, those disclosed in the following publications:

U.S. Pat. Nos. 7,396,662, 7,393,833, 7,385,036, 7,285,631, 7,279,296, 7,208,291, 7,189,809, 7,041,474, 6,936,692, and 6,312,922;

U.S. Patent Publication Nos. 20050089470, 20050089471, 20070264194, 20070253901, 20080260650, and 20080193376; and Ishino et al., 2008, J. Nucl. Med., 49:1677-1685 and Hag et al., 2008, BBRC, doi:10.1016/j.bbrc.2008.10.037 (available online Oct. 18, 2008).

In accordance with one embodiment a non-invasive method of in vivo imaging of atherosclerotic plaques in a mammalian species is provided. In one embodiment the mammalian species is a human patient. The method comprises the steps of administering a LOX-1 imaging composition to the patient, waiting for a sufficient amount of time to allow the imaging component to bind to LOX-1 sites in vivo and the remaining non-bound imaging component to be cleared from the body (or at least be localized to the liver, kidneys and other organs responsible for clearing compounds from the bloodstream), and then imaging the relevant tissues (e.g. the vascular system). The imaging agent is formulated for intravenous administration and is combined with suitable pharmaceutically acceptable carriers.

In accordance with one embodiment the tissues are images approximately 24 hours after administration of the LOX-1 imaging composition to the patient. However, the amount of time between administration and the step of imaging will vary depending on the patient and the specific imaging component that was administered. In one embodiment the scanning step is conducted between 1 and 30 hours after administration of the imaging composition, however, the imaging step can be conducted anytime within a range of 1 to 3, 1 to 12, 8 to 36, 12 to 72, 20 to 48, 24 to 48, 24-36 or 24-30 hours after administration. After the appropriate interval, the patient is then scanned using the relevant MRI, SPECT, PET, CT techniques known those skilled in the art to detect localization of the imaging composition and thus image the associated atherosclerotic plaques. In accordance with one embodiment the scanning step comprises spiral magnetic resonance spectroscopic imaging of the patient administered the LOX-1 imaging composition. Advantageously, the present method detects atherosclerotic plaques that are active in taking up ox-LDL and therefore identifies those plaques that are at highest risk of rupturing. Accordingly, this analysis can identify patients at high risk for myocardial ischemia, acute myocardial infarction and stroke and can assist in determining an appropriate therapeutic response.

In accordance with one embodiment the imaging component used in the screening methods disclosed herein comprises an antibody that specifically binds to the LOX-1. The antibody is linked either directly or indirectly to a marker that is detectable in vivo. In one embodiment the detectable maker is an MRI contrast agent and in an alternative embodiment the marker is SPECT contrast agent. In one embodiment the LOX-1 antibody is linked to the marker via a liposome, wherein both the antibody and the detectable marker are covalently linked to exterior surface of the liposome. In one embodiment the liposome comprises both an MRI and a SPECT contrast agent linked to said liposome in addition to the linked LOX-1 antibody. In another embodiment a LOX-1 imaging composition is administered wherein the composition comprises a mixture of liposomes, wherein different subsets of liposomes are present in the composition that differ from one another by the presence of a different detectable marker.

In one embodiment the LOX-1 imaging composition comprises two or more different liposomes, wherein the subsets of liposomes differ in having different MRI contrast agents. In one embodiment the MRI contrast agents are selected from the group consisting of Gadolinium-based contrast agents, 19 Fluorine-based contrast agents and iron oxide particles. For example in one embodiment the LOX-1 imaging composition comprises one set of liposomes that are decorated with a Gadolinium-based contrast agent and a second set of liposomes decorated with a 19 Fluorine-based contrast agent. In another embodiment LOX-1 imaging composition comprises one set of liposomes decorated with an MRI contrast agent and a second set of liposomes decorated with a SPECT contrast agent. In one embodiment the liposomes are decorated with one or more SPECT contrast agents selected from the group consisting of $^{111}$In and $^{123}$I. In one embodiment the LOX-1 imaging composition further comprises a fluorescent detection agent linked to said liposome.

In those embodiments where the LOX-1 imaging composition comprises multiple detection modalities (either as the result of having two different detectable markers on each liposome or as the result of the composition comprising a mixture of liposomes that differ from one another based on the detectable marker attached to the individual liposome), the scanning step may include scanning for both detectable markers. For example, in one embodiment the scanning step is conducted using a dual modality scanner to detect both a MRI and the SPECT contrast agent, or some other combination of MRI, PET or SPECT contrast agents. Alternatively, in one embodiment the scanning step comprises a series of scans to first detect either the MRI, PET or SPECT contrast agent, followed by a second and even a third scan to detect the other contrast agent(s).

In accordance with one embodiment a method of assessing a patient's responsiveness to a cholesterol lowering therapy or a plaque stabilization therapy is provided. In accordance with one embodiment the patients cholesterol levels are monitored after receiving a lipid-lowering therapeutic agent selected from the group consisting of bile acid-binding resins, niacin, 3-hydroxy-3-methylglutaryl-coenzyme A (HMG-CoA) reductase inhibitors (e.g. a statin). In one embodiment the total number of atherosclerotic plaques, and more importantly the number of atherosclerotic plaques actively taking up ox-LDL, are measured by in vivo scanning of the patient's vascular tissue both before and after administration of a therapeutic regiment to determine the efficacy of the administered therapy. Further supplementation or alteration of the cholesterol lowering therapy can be conducted based on the results of the analysis.

According to one embodiment the method of monitoring a patient's response to a cholesterol lowering or a plaque stabilization therapy comprises the steps of administering to said patient a first dose of a LOX-1 imaging composition, wherein said LOX-1 imaging composition comprises a carrier (such as a small peptide, liposome or micelle having a diameter of less than 100 nm), a LOX-1 targeting agent (e.g., an anti-LOX-1 antibody) linked to said carrier; and an in vivo detection reagent linked to the carrier wherein the detection agent is selected from the group consisting of PET, MRI and SPECT contrast agents. After administration of the first dose of the LOX-1 imaging composition and after waiting for sufficient time to pass to allow the imaging component to bind to its intended target, the patient is scanned to provide a first image of the associated atherosclerotic plaques. The patient then receives the cholesterol lowering therapy for a predetermined length of time, followed by administering to the patient a second dose of the LOX-1 imaging composition. The patient is then scanned a second time to detect localization of the imaging composition and thus providing a second image of atherosclerotic plaque. Comparison of the first and second image of atherosclerotic plaques reveals if the number of atherosclerotic plaques, or at least the number of atherosclerotic plaques actively taking up ox-LDL (i.e., plaque vulnerable to rupturing), has decreased over the course of administration of said cholesterol lowering therapy. In one embodiment the method is used to assess the patient's responsiveness to the administration of one or more statins.

In another embodiment a system for screening for new drugs is provided. The system comprises the use of an animal model that is administered a candidate therapeutic compound wherein the animal model is subjected to an in vivo scan, using a LOX-1 imaging composition disclosed herein, before and after administration of the candidate compound. In one embodiment the candidate therapeutic agent is a potential lipid lowering agent, an anti-inflammatory agent or a plaque stabilizing drug. In one embodiment the animal model is a mouse or rat and in one embodiment the animal model is a LDLR−/− mouse.

In accordance with one embodiment a method of screening a compound for in vivo activity as either a lipid lowering, plaque stabilizing or anti-inflammatory agent is provided. The method comprises the steps of administering to an animal model system a first dose of a LOX-1 imaging composition, wherein said LOX-1 imaging composition comprises a carrier (e.g., a liposome or micelle having a diameter of less than 100 nm), a LOX-1 targeting agent (e.g., an anti-LOX-1 antibody) linked to said carrier; and an in vivo detection reagent linked to the carrier wherein the detection agent is selected from the group consisting of PET, MRI and SPECT contrast agents. After administration of the first dose of the LOX-1 imaging composition and after waiting for sufficient time to pass to allow the imaging component to bind to its intended target, the animal model system is scanned to provide a first in vivo image of the associated atherosclerotic plaques. The animal model system then receives the lipid lowering, plaque stabilizing or anti-inflammatory agent for a predetermined length of time, followed by administering to the animal model system a second dose of the LOX-1 imaging composition. The animal model system is then scanned a second time to detect localization of the imaging composition, and thus providing a second image of atherosclerotic plaque. In one embodiment the animal model system is scanned multiple times throughout the administration of the therapeutic agent, or alternatively a single scan is conducted after completion of the therapeutic regiment. Comparison of the first pretreatment in vivo scan results to the subsequent in vivo scans conducted after administration of the potential therapeutic agent allows for the determination of the in vivo effectiveness of administered composition. Efficacy of the test compound can be determined by an improvement in the plaque stability, a reduction is lipid levels, a reduction in plaques taking up ox-LDL or other detectable quantitative or qualitative parameters. In accordance with one embodiment the animal model system is an atherosclerotic animal model system, and in one embodiment the animal model system is a mouse, including for example, LDLR−/− mice.

Example 1

Cardiovascular Magnetic Resonance (CMR) Based Molecular Imaging of LOX-1

Oxidized low-density lipoprotein and its receptor LOX-1 play a crucial role in the initiation, progression, and destabilization of atherosclerotic lesions. A noninvasive tool to improve the clinical characterization of this pathological process is needed. The following study indicates the feasibility of CMR based molecular imaging compositions targeted to LOX-1 which is highly expressed on atherosclerotic lesions in mice.

Materials and Methods:

LDLR−/− mice on an atherogenic diet for >16 weeks were used. The imaging probe consisted of liposomes decorated with anti-LOX-1 antibody (or nonspecific IgG), gadolinium, and DiI fluorescence markers. MRI at 7.0 T (Clinscan, Bruker/Siemens) was performed at baseline and 24 hrs after intravenous injection of 150 ml of probe containing LOX-1 antibody (n=7) or nonspecific IgG (nIgG) (n=5) with 0.075 mmol Gd/kg, followed by excision of the aorta for frozen cross-sections. The fluorescence image used to indicate whether the probe bound to the plaque was examined under fluorescence microscopy.

MRI of the ascending aorta was performed with a T1-weighted black-blood spiral gradient-echo sequence (echo time, 1.2 ms; flip angle, 90°; field of view, 3×3 cm; 135 interleaves; readout window, 4.1 ms; spatial resolution, 67 mm)) with 11 contiguous 0.5 mm-thick slices. Four signal averages with cardiac and respiratory gating were used, for a total imaging time of 2.5 minutes per slice. For the post-injection scan, the slices were matched to the baseline preinjection scan by using the left main and LAD coronary artery as anatomic landmarks. To quantitatively analyze the MRI results, signal intensity (SI) was measured in 4 regions of interest within the aortic wall as well as the aortic lumen and muscle on each slice at both time points. The standard deviation of noise was also recorded for each slice. These measurements were recorded for all slices at every time point imaged. The contrast-to-noise ratio (CNR) of aortic wall to lumen was calculated for each slice. % CNR=(CNRpost−CNRprecontrast)/CNRprecontrast. The normalized enhancement ratio (NER) was defined as the average post-contrast SI from 4 regions of interest within the aortic wall divided by the muscle SI in the same slice and then divided by the pre-contrast SI. % NER=(NER−1)'100.

Figure 1A:
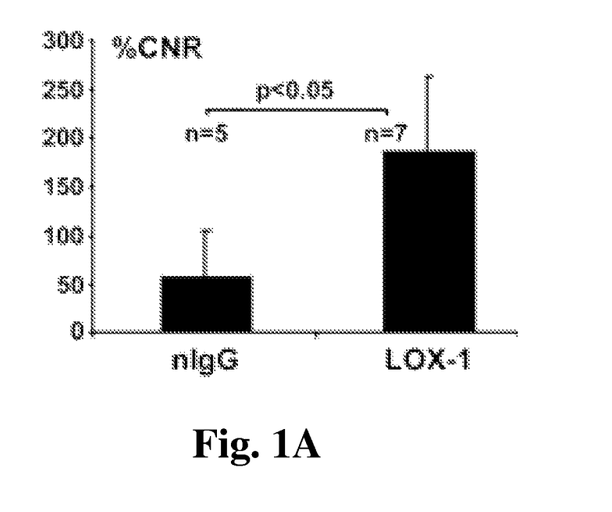
FIGS. 1A & 1B are bar graph depictions of the MRI data produced by LDLR−/− mice injected with LOX-1 antibody probe or nIgG probe. The % contrast to noise ratio (CNR) was significantly higher at 24 hours in LDLR−/− mice that received the probe with LOX-1 antibody compared to nIgG (187.4±71.5% vs. 58.4±46.9%, p<0.05, FIG. 1A). The % normalized enhancement ratio (NER) was also significantly higher at 24 hours in LDLR−/− mice that received the probe with LOX-1 antibody compared to nIgG (121.1±38.9% vs. 18.4±13.9%, p<0.01, FIG. 1B). The atherosclerotic lesions were similar between the 2 groups as determined by H&E staining of aortic cross-sections.
Figure 1B:
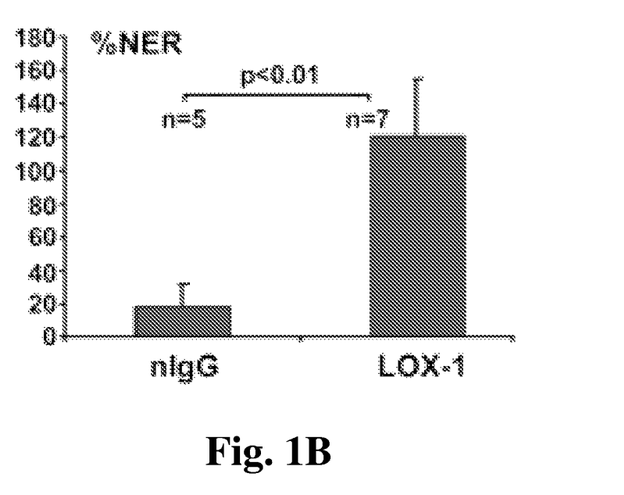

Results:

Fluorescence imaging found that the LDLR−/− mice injected with the LOX-1 antibody probe showed significant uptake in atherosclerotic plaque. There was little fluorescence signal in atherosclerotic plaques in LDLR−/− mice that received the control nIgG probe. The MR images consistently showed strong post-contrast signal on atherosclerotic plaques at 24 hours in LDLR−/− mice injected with LOX-1 antibody probe, but not those injected with nIgG probe. The % CNR was significantly higher at 24 hours in LDLR−/− mice that received the probe with LOX-1 antibody compared to nIgG (187.4±71.5% vs. 58.4±46.9%, p<0.05, FIG. 1A). Accordingly, the % NER was also significantly higher at 24 hours in LDLR−/− mice that received the probe with LOX-1 antibody compared to nIgG (121.1±38.9% vs. 18.4±13.9%, p<0.01, FIG. 1B). The atherosclerotic lesions were similar between the 2 groups as determined by H&E staining of aortic cross-sections (G&H).

Conclusions:

MRI with liposomes containing gadolinium and LOX-1 antibody demonstrates specific targeting of atherosclerotic plaques with high contrast to noise ratios. Spiral imaging produced high spatial resolution without motion artifacts and black blood imaging improved visualization of vessel wall.

Example 2

Radiolabel Based Molecular Imaging of LOX-1

In the following experiment a novel radio labeled imaging probe targeted to LOX-1 was used to assess the presence of atherosclerosis plaques.

Materials and Methods:

20 Apo E−/− mice on Western diet for >20 weeks were used for this experiment. The targeted imaging probe (TP) consisted of liposomes decorated with anti-LOX-1 antibody, $^{111}$In and DiI fluorescence markers. Control probe (CP) carried nonspecific IgG. 24 hrs after iv probe injection, 5 mice per group were used for ex vivo fluorescence microscopy. The other 5 mice were used for microSPECT/CT, followed by ex vivo aorta phosphor imaging.

Results:

The in vitro binding study demonstrated selective probe targeting to LOX-1. In vivo fluorescence imaging showed that the targeted imaging probe, but not control probe, bound mainly to the shoulder area of some plaques. The targeted imaging probe signal in plaques was co-localized with the areas of apoptosis and elevated MMP9 expression. MicroSPECT imaging showed hotspots in the aortic arch in all the targeted imaging probe injected mice (n=5) corresponding with focal uptake areas observed by phosphor imaging of the excised aortas. Little control probe was bound to plaques as detected by fluorescence, microSPECT or phosphor imaging.

Conclusions:

LOX-1 can be used as a target for molecular imaging of atherosclerotic plaque using a novel radiolabeled imaging probe. Imaging of LOX-1 may also predict plaque vulnerability.

Example 3

Single Photon Emission Computed Tomography (SPECT)

The following results show the imaging probe disclosed herein can be used to specifically detect the expression of the LOX-1 to oxidized LDL in the in vivo setting using SPECT/CT. Five cholesterol fed apoE knockout mice were imaged after being injected with a fluorescent and $^{111}$In-labeled LOX-1 targeted imaging probe using in vivo SPECT/CT. The signal seen during non-invasive imaging was strongly related to the presence of atherosclerotic plaque as determined by ex vivo Phosphor imaging and to LOX-1 expression as determined by fluorescence microscopy. Importantly, when a non-specifically targeted molecular imaging probe was used, no signal was seen using in vivo SPECT/CT or ex vivo phosphor imaging. Serial blood sampling analysis revealed that the ideal time to image the mice is approximately 24 hours after injection of the imaging probe due to low background blood pool activity of the radiotracer at that time.

Ultrasound

The LOX-1 antibody was decorated with microbubbles and used to detect the target LOX-1 antigen. The labeling process of the LOX-1 antibody did not affect the binding activity to the LOX-1 antigen according to in vitro binding analysis. In a flow chamber study, we found that the microbubble-LOX-1 antibody attached to the target LOX-1 antigen at a physiological shear stress with maximal stress at 0.58 dynes/cm$^2$. A Philips HDI5000 ultrasound scanner was used to image the intended vasculature in a mouse model. Even with the relatively modest spatial resolution of this scanner (0.25 mm), the aorta and carotid arteries were visualized in ultrasound images. Applicants anticipate that LOX-1-antibody-targeted microbubbles can be used for in vivo analysis by enhancing the resolution of the ultrasound scanner. The scanner, vevo 770, used in the above described experiment is capable of spatial resolution better than 0.1 mm, and up to 100 fps frame rate. Further resolution upgrades will improve the bubble detection capability while suppressing background tissue signal. The spatial resolution will then be approximately the same as MRI, which should allow detection at the different areas of individual plaques, as in histology.

Example 4

Many studies have demonstrated that oxidized low density lipoprotein (ox-LDL) plays a critical role in atherogenesis. The pathological effects of LOX-1 not only initiate atherosclerotic lesion formation, but also contribute to the vulnerability of a plaque to rupture.

The following experiment demonstrates that a novel non-invasive imaging probe targeted to LOX-1 can be used to detect atherosclerotic lesions in vivo using hybrid SPECT/CT and MRI.

Materials and Methods
Imaging Probe

Liposomes consisted of 1,2-Dioleoyl-sn-Glycero-3-Phosphocholine (Avanti Lipids, Alabaster, Ala.), cholesterol (Sigma), N-hydroxysuccinimide ester of carboxy-PEG3400-DSPE (Shearwater Polymers) and DiI (Invitrogen) at the mass ratio of 50:25:25:1. If liposomes were used to make imaging probes for MRI study, diethylenetriaminepentaacetic acid α,ω-bis(8-stearoylamido-3,6-diaoxaoctylamide)gadolinium complex (Sigma) was added as 1:1 mass ratio with phosphatidylcholine. Lipids were completely dissolved in chloroform and subjected to rotary evaporation in a glass vial under vacuum to create a thin uniform layer of dry lipid on the glass surface. Citrate buffer (10 mM, pH 4.4) was quickly added, mixture agitated to prepare multilamellar liposomes, and then rapidly passed through a 100 nm filter 40 times using a Liposofast device (Avestin). Liposomes (~100 nm in size) were immediately mixed with LOX-1 or nonspecific IgG antibody (R&D Systems, 250 μg in 10 mM HEPES buffer, pH 8.0) overnight at 4° C., so that covalent coupling between the protein amino group and activated carboxyl of PEG-lipid would occur. The compounds were subjected to repeated ultracentrifugation at 45,000 rpm (50Ti rotor, Beckman Coulter ultracentrifuge) for 30 min to remove free antibodies. Finally the immunoliposome pellets (probes) were dispersed in PBS buffer.

For $^{111}$In labeling, liposomes carried a trace amount of DTPA-phosphatidylethanolamine. The liposome preparations were mixed with $^{111}$In (Perkin Elmer Life Sciences) in acetate acid buffer (0.5 M, pH 6.0) for 2 hrs at room temperature and then filtrated by a single passage through a Sephadex G50 gel column with a centrifuge at 1000 g for 1 min. The imaging probe consisted of liposomes decorated with anti-LOX-1 antibody (called LOX-1 probe) or non-specific nIgG (called nIgG probe), $^{111}$Indium for SPECT (or Gadolinium for MR imaging) and DiI fluorescence markers.

Dot Blot Analysis

LOX-1 antigen (R&D system) (200 ng) was placed on a nitrocellulose membrane, dried, and blocked with 3% BSA for 1 hr. The membranes were incubated with serial dilutions (0.06 to 4 nM LOX-1 antibody concentrations) of $^{111}$In-liposome-LOX-1-Ab-DiI at room temp for 2 hrs, and then exposed to a phosphor imaging plate for 90 min, followed by gamma well counting for each dot.

Solid Phase Binding Assay

LOX-1 antigen (200 ng in 0.1 ml PBS) was placed into each well of a standard 96-well ELISA plate overnight, washed with PBS, and then blocked with 3% BSA for 1 hr. Serial dilutions (0.1 to 14 nM LOX-1 antibody concentrations) of Gd-liposome-LOX-1-Ab-DiI were added to each well and incubated at room temp for 2 hrs. The plate was washed with PBS 4 times. Fluorescence intensity of antigen-bound liposomes was determined with a microplate reader (Gemini XS, Molecular Devices). A control probe experiment with Gd-liposome-nIgG-DiI was performed in parallel to evaluate nonspecific binding.

Animal Protocol

ApoE$^{-/-}$ mice, purchased from Jackson Laboratories, were placed on Western diet (Harlan) for over 20 weeks and used for SPECT imaging. Mice were anesthetized with isoflurane and injected intravenously with 150 μL of LOX-1 or nIgG probe with ~600 μCi of $^{111}$In. SPECT/CT imaging was performed at 24 hrs after injection. The aortas were excised following the SPECT/CT study. Some aortas (n=6) were longitudinally opened and then exposed to phosphor imaging plate for 90 min, followed by Sudan IV staining to identify atherosclerotic lesions. Other aortas (n=6) were fixed with 4% paraformaldehyde overnight and sent to the UVA Core Pathology Laboratory for analysis of frozen sectioning.

LDLR$^{-/-}$ mice, purchased from Jackson Laboratories and kept on an atherogenic diet (Harlan) for 16 weeks, were used for the MRI study. Mice were anesthetized with isoflurane and intravenously injected with 150 μL of LOX-1 (n=7) or nIgG probe (n=5) with 0.075 mmol Gd/kg. LDLR$^{-/-}$/LOX-1$^{-/-}$ double knockout mice, generated as described previously (Li et al. Circulation. 2003; 107:612-7), were injected with 150 μl of LOX-1 probe (n=5) with 0.075 mmol Gd/kg. MR imaging (7.0T, Clinscan, Bruker/Siemens) was performed at baseline and then 24 hrs after injection. The aortas were excised following MRI for frozen sectioning. Frozen sections were used to examine binding of probe in the atherosclerotic plaques and for H&E and immunostaining Blood Pool Clearance and Tissue Biodistribution of Probes Wild-type C57BL/6 mice were anesthetized with isoflurane and intravenously injected with the LOX-1 (n=3) or nIgG (n=3) probe with ~600 μCi of $^{111}$In. Five μl of blood was collected at different time points (15 sec, 30 sec, 1 min, 15 min, 30 min, 1 h, 2 h, 4 h and 24 h) from the tail vein. The radioactivity of blood pool was normalized based on the radioisotope decay factor of $^{111}$In and then divided by initial blood pool counts for blood pool clearance. Apo E$^{-/-}$ mice were intravenously injected with LOX-1 (n=5) or nIgG (n=3) probe with ~600 µCi of $^{111}$In. Blood was collected at the above-mentioned time points. At 24 hours after injection, tissues from heart, lung, liver, fat, muscle, kidney, spleen and gut, and urine were collected. Tissue radioactivity was calculated by γ-counts per mg tissue wet weight per time unit and then divided by blood pool radioactivity at 24 hrs after injection. Aortas were excised and used for frozen sections.

Confocal Microscopy

Frozen aortic sections were washed of dextrose with PBS buffer and blocked with 3% BSA for 1 hr, and then incubated with a FITC adsorbed rabbit anti-mouse macrophage antibody (1:50 dilution, Cedarlane Laboratories) and a Dylight 633 Red (Thermo Scientific) labeled goat anti-mouse antibody to smooth muscle cells (1:100 dilution, Santa Cruz) diluted in 3% BSA overnight at 4° C. The sections were then washed in PBS buffer 4 times for 5 min each time and incubated with DAPI (1 µg/ml) for 10 min. The sections were washed again with PBS and mounted with anti-fade medium. Confocal imaging was performed within 24 hrs using a Zeiss LSM 510 META microscope in an inverted configuration. This system is equipped with four lasers: a 405 nm blue diode, an Argon (488 nm), a green HeNe (543 nm) and a red HeNe (633 nm). The system contains two confocal detectors, one confocal META detector and a transmitted light detector. The detectors were configured for blue, green, red and far-red emission detection (filters: band pass 420-480 nm, 505-530 nm, 560-615 nm and 650 nm). Pinhole settings were adjusted for equal "optical sections".

Fluorescent TUNEL Staining

In situ nick end-labeling (TUNEL) and propidium iodide staining was performed as described previously (Li et al. J Cardiovasc Pharmacol Ther. 2002; 7:147-53). In brief, frozen sections on slides were incubated with 0.3 U/µl terminal deoxynucleotidyl transferase (TDT) and 0.04 nmol/µl fluorescein-12-dUTP (Promega) in TDT buffer for 60 min at 37° C. Unincorporated fluorescein-dUTP was removed, and the slides were immersed in 1 µg/ml of propidium iodide in PBS for 15 min. The negative controls were performed without TDT enzyme.

Fluorescent Immunostaining

Details of immunostaining have been provided previously (Li et al. J Cardiovasc Pharmacol Ther. 2002; 7:147-53). In brief, 5 µm thick frozen sections from aortas were incubated with rabbit anti-mouse MMP9 antibody (sc-6840, Santa Cruz) overnight at 4° C. Sections were rinsed in PBS buffer 4 times, and incubated with secondary antibody goat anti-rabbit IgG-FITC (Santa Cruz). Sections were rinsed with PBS buffer 4 times and then mounted with anti-fade medium. The negative controls were prepared using secondary antibody alone.

SPECT/CT Imaging Protocol

SPECT/CT imaging was performed using a dual-head camera with 1 mm pinhole aperture. A complete SPECT data set consisted of 60 projections at 6 degree increments at 30 sec per projection. The images were reconstructed using customized software with a maximum-likelihood expectation maximization (MLEM) algorithm. To identify the position of the aorta, CT was performed before (without contrast) and after (with contrast) SPECT imaging. A complete CT data set consisted of 216 projection images acquired at one degree increments over 5 minutes. The intravascular agent Fenestra® (Cat# LC-131, ART Inc.) was used to provide CT contrast.

MRI Scan Protocol

MRI of the ascending aorta was performed with a T1-weighted black-blood spiral gradient-echo sequence (echo time 1.2 ms; flip angle 90°; field of view 3×3 cm; 135 interleaves; readout window 4.1 ms; spatial resolution 67 µm) with 11 contiguous 0.5 mm-thick slices. Cardiac-gated double-inversion pulses for suppression of the blood signal were interleaved with cardiac-gated spiral readouts, resulting in an effective repetition time for the readouts of two R-R intervals. Four signal averages with cardiac and respiratory gating were used, for a total imaging time of 2.5 minutes per slice. For the post-injection scan, the slices were matched to the baseline pre-injection scan using the origin of the left main and LAD coronary artery as anatomic landmarks.

To quantitatively analyze the MRI results, signal intensity (SI) was measured in 4 regions of interest within the aortic wall as well as the aortic lumen and muscle on each slice at both time points. The standard deviation of noise was also recorded for each slice. These measurements were recorded for all slices at every time point imaged. The contrast-to-noise ratio (CNR) of aortic wall to lumen was calculated for each slice. % CNR=(CNR post−CNR pre-injection)/CNR pre-injection. The normalized enhancement ratio (NER) was defined as the average post-contrast SI from 4 regions of interest within the aortic wall divided by the muscle SI in the same slice and then divided by the pre-contrast SI. % NER=(NER−1)×100. In this study, % CNR and % NER were used to present the summarized MRI data.

Data Analysis

Data represent mean of at least three independently performed experiments. Data are presented as mean±SD. Data were analyzed by ANOVA, followed by a Bonferroni correction. A P value of less than 0.05 was considered to be statistically significant.

Results

Binding Analysis of Probes In Vitro

Figure 2A:
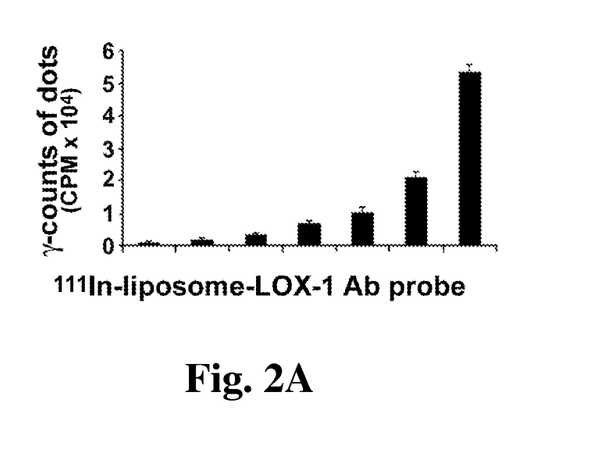
Figure 2B:
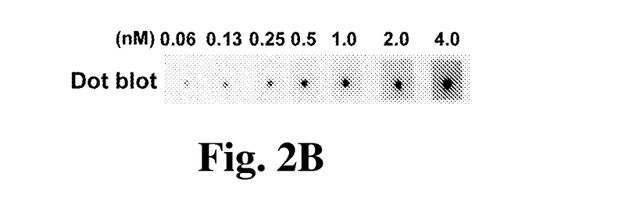
FIG. 2B presents a dot blot analysis representative of data generated. The graph of FIG. 2A represents summarized data from 3 separate experiments.
Figure 2C:
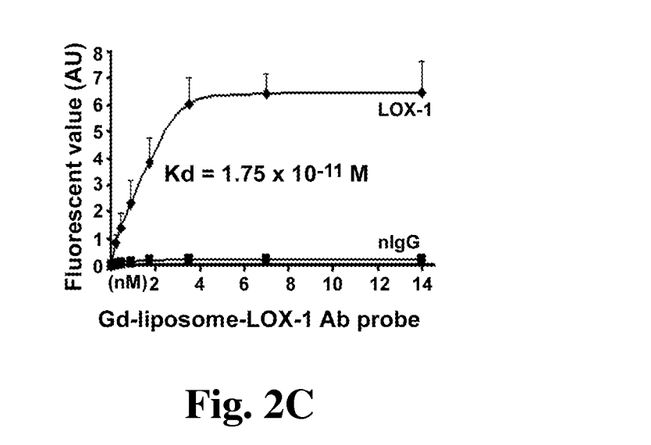
FIG. 2C is a graph of experimental data showing that LOX-1 probe (Gd-liposome-LOX-1 antibody-DiI) bound to LOX-1 antigen in vitro by ELISA. The non-specific IgG (nIgG) probe (Gd-liposome-nIgG-DiI) showed no binding to LOX-1 antigen (n=3).

As shown in FIG. 2A, anti-LOX-1 antibody-linked liposomes successfully bound to LOX-1 antigen-coated surfaces. This was demonstrated by Dot blot analysis using the LOX-1 probe ($^{111}$In-liposome-LOX-1 antibody-DiI) (FIG. 2B). Fluorescence-labeled solid phase binding assay also showed that the LOX-1 probe (Gd-liposome-LOX-1 antibody-DiI) bound to LOX-1 antigen in a sigmoid curve pattern, whereas, the nIgG probe (Gd-liposome-nIgG-DiI) showed very little binding to LOX-1 antigen (FIG. 2C).

Blood Pool Clearance and Tissue Bio-Distribution In Vivo

Figure 3A:
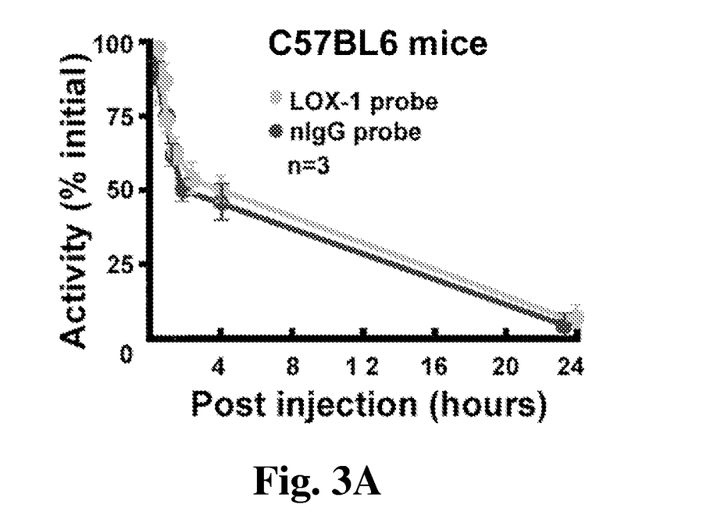
FIGS. 3A & 3B provide graphs of experimental data showing blood pool clearance of probes in mice. LOX-1 and nIgG probes had similar clearance rate in blood in wild type C57BL6 mice (FIG. 3A). LOX-1 probes cleared slowly compared to nIgG probes in the Apo E−/− mice. However, there was no significant difference in clearance between the two probes at 24 hrs (FIG. 3B).
Figure 3B:
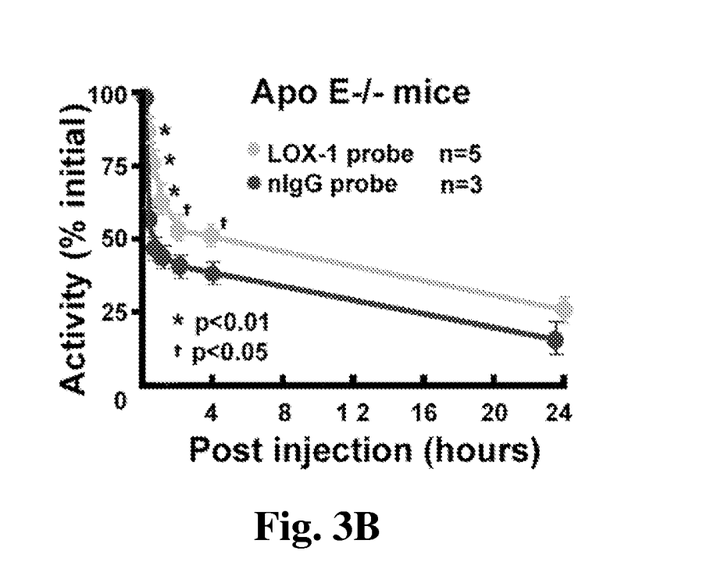

LOX-1 and nIgG probes had similar blood clearance rate in wild type C57BL/6 mice (FIG. 3A). However, LOX-1 probes cleared more slowly than nIgG probes initially after injection (P<0.05 at different time points) in the ApoE$^{-/-}$ mice. There was no significant difference in clearance of the two probes at 24 hours post-injection (FIG. 3B). As expected, both probes largely accumulated in the liver and spleen because of their liposome nature and the presence of Fc fragments on the antibody or IgG molecules on the liposome surface. Table 1 shows tissue bio-distribution. LOX-1 probes are accumulated in liver and spleen.

TABLE 1

Bio-distribution of LOX-1 probe in Apo E−/−mice (% 24 hr blood activity)

| Lung | Heart | Kidney | Spleen | Muscle | Liver | Fat | Gut | Urine |
|---|---|---|---|---|---|---|---|---|
| 52 ± 15 | 19 ± 4 | 37 ± 12 | 933 ± 108 | 8 ± 4 | 837 ± 284 | 4 ± 3 | 7 ± 2 | 9 ± 04 |

LOX-1 Expression, LOX-1 Probe Binding in Plaque In Vivo

Figure 4A:
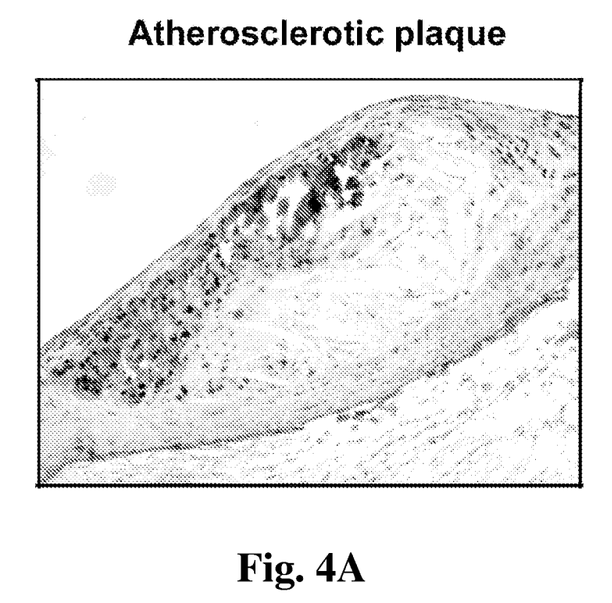
FIGS. 4A & 4B are histological stains demonstrating LOX-1 expression and LOX-1 probe binding in atherosclerotic plaque. LOX-1 is highly expressed in atherosclerotic plaques, especially in the shoulder area of the plaque. A large amount of LOX-1 probe is bound to the shoulder area of the atherosclerotic plaque, and a small amount is bound to the plaque cap (L=lumen).
Figure 4B:
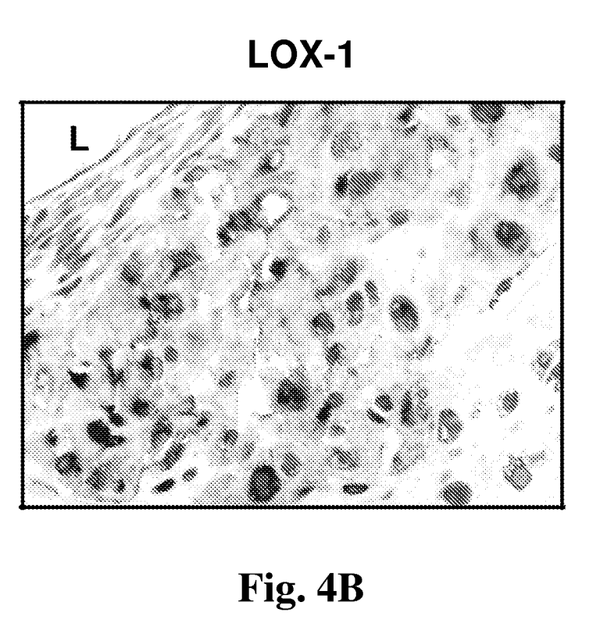

We found that LOX-1, determined by immunostaining, is highly expressed in atherosclerotic plaques, especially in the shoulder area of the plaque (FIGS. 4A & 4B). To demonstrate the binding of probe to plaque in vivo, Apo E$^{-/-}$ mice were given LOX-1 or nIgG probes and aortas excised at 24 hrs after injection. Most of the LOX-1 probe binding was observed in the shoulder area of the atherosclerotic plaque. Some binding of the LOX-1 probe to the cap of the plaque was also observed. This LOX-1 probe binding in plaque in vivo is consistent with the expression of LOX-1 in atherosclerotic plaques. Notably, the LOX-1 probe did not bind to every atherosclerotic plaque in vivo. In contrast to the extensive binding of LOX-1 probe to the atherosclerotic region, negligible nIgG probes binding to the atherosclerotic plaque was noted in vivo.

Co-Localization of LOX-1 Probe Binding to Cells within Atherosclerotic Plaque In Vivo To further characterize specific cell lines within the plaque to which LOX-1 probe binds, fluorescent immunostaining was performed for macrophages and smooth muscle cells in frozen aortic sections taken from Apo E$^{-/-}$ mice injected with LOX-1 probes. Confocal microscopy showed that a vast amount of LOX-1 probe co-localized with macrophages in the atherosclerotic plaque. There was much less LOX-1 probe co-localization with proliferated smooth muscle cells.

LOX-1 Probe Binding, Apoptosis and Matrix Metalloproteinase 9

Next, we examined the relationship between the in vivo LOX-1 imaging signal and other typical markers of a vulnerable plaque including apoptosis and MMP9 expression. LOX-1 probe binding was co-localized with apoptotic cells as well as MMP9. Notably, there were few apoptotic cells or little MMP9 expression in regions of the plaque with minimal or no LOX-1 probe binding.

SPECT/CT Imaging, Phosphor Imaging and Sudan IV Staining

The SPECT/CT scan was performed at 24 hrs after injection of probes based on blood pool clearance of probes. After in vivo imaging, the aortas were excised and longitudinally cut and ex vivo phosphor imaging was performed. Sudan IV staining was then performed to determine the extent and location of atherosclerotic lesions. There were no hotspots detected by SPECT imaging in Apo E$^{-/-}$ mice injected with nIgG probe. Likewise, there were no hotspots observed on the ex vivo phosphor plate images. In contrast, all mice injected with LOX-1 probe had hotspots in the atherosclerotic region of the aortic arch. These findings were further confirmed by hotspots in the aortic arch on ex vivo phosphor imaging. There were no differences in the extent of atherosclerotic lesions between two groups determined by Sudan IV staining.

MR Imaging, Fluorescence Imaging and H&E Staining

Figure 5A:
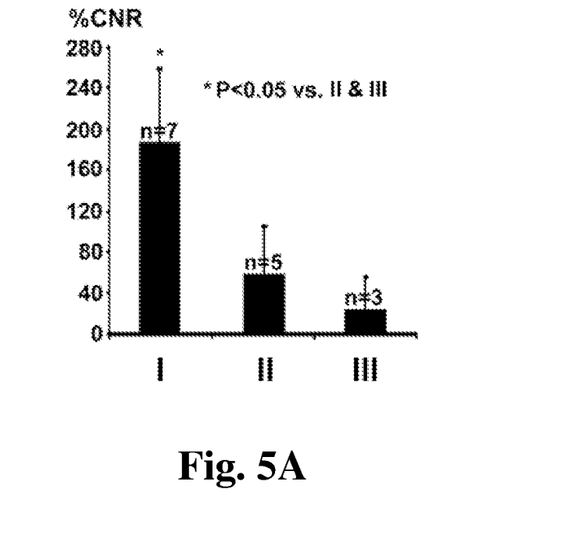
Figure 5B:
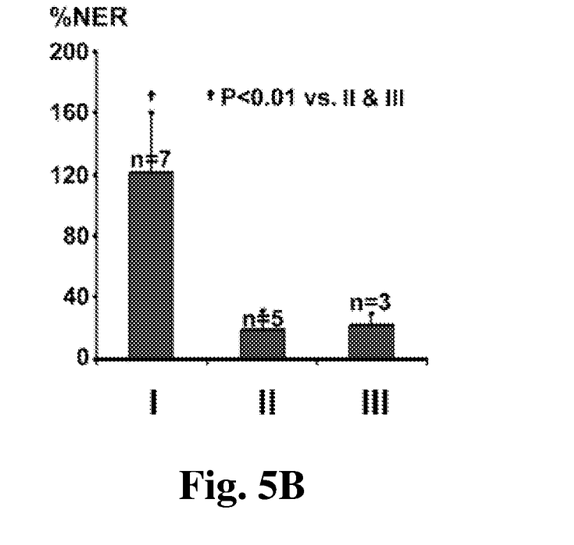

MRI was performed at 24 hrs after injection of probes. By MRI, strong post-injection gadolinium enhancement was visualized in the aortic root and the arch in LDLR$^{-/-}$ mice injected with LOX-1 probe. These findings were confirmed by ex vivo fluorescence imaging of frozen sections that showed LOX-1 probe binding in the same area of atherosclerotic plaque as the finding of in vivo MR imaging. The size of atherosclerotic plaque was confirmed by H&E staining Of note is the fact that post-Gd enhancement was not seen in the LDLR$^{-/-}$ mice injected with nIgG probe. There was very little nonspecific nIgG probe binding to the plaque. The specificity of LOX-1 probe binding to plaque and subsequent post-Gd enhancement was further confirmed by using LDLR$^{-/-}$/LOX-1$^{-/-}$ double knockout mice. LDLR$^{-/-}$/LOX-1$^{-/-}$ mice injected with LOX-1 probe did not show any post-Gd enhancement or any LOX-1 probe binding to plaque. These mice showed less atherosclerotic lesions on H&E staining in concert with previous studies (Li et al. *Circulation*. 2003; 107:612-7). The summarized MRI data showed that LDLR$^{-/-}$ mice injected with LOX-1 probe had significantly higher contrast to noise ratio (CNR; see FIG. 5A) and normalized enhancement ratio (NER; see FIG. 5B) than the other two control groups LDLR$^{-/-}$ mice injected with nIgG probe and LDLR$^{-/-}$/LOX-1$^{-/-}$ mice injected with LOX-1 probe.

Discussion

Specific non-invasive techniques are needed to detect atherosclerotic plaque vulnerability and to monitor changes in these parameters. Development of such approaches requires delineation of appropriate markers of atherosclerosis and use of non-invasive imaging tags directed at these markers. To date, most invasive (intravascular ultrasound) and noninvasive (CT angiography) techniques for plaque imaging identify only the presence and extent of atherosclerotic plaque and do not image specific targets related to vulnerability.

Several studies have suggested that activation of the ox-LDL receptor LOX-1 induces endothelial dysfunction, enhances ox-LDL uptake in monocytes/macrophages and induces a state of oxidative stress. Accordingly, it has been suggested that LOX-1 is involved in the initiation and progression of atherosclerotic plaque. Indeed, recent studies show that deletion of LOX-1 reduces the progression of atherosclerosis (Mehta et al. Circulation Research, 2007; 100: 1634-1642). Furthermore, LOX-1 activates Matrix Metalloproteinases (MMPs) which are responsible for collagen degradation and initiation of plaque rupture, the most proximate cause of acute coronary syndromes. Circulating levels of soluble LOX-1 have also been observed to be increased in patients with unstable coronary syndromes.

The data presented herein validates the molecular imaging of LOX-1 protein to detect atherosclerotic plaque using SPECT/CT and MR imaging techniques in two different models of atherosclerosis, the Apo E$^{-/-}$ and LDLR$^{-/-}$ mice on a high cholesterol diet. LOX-1 imaging probe administered intravenously can specifically bind to atherosclerotic plaques, especially in the cap and shoulder areas. Both SPECT/CT and MR imaging clearly detected atherosclerotic plaques in the aortic arch using the LOX-1 imaging probe. Importantly, the LOX-1 signal in the atherosclerotic plaque was found to co-localized with macrophages, apoptotic cells and MMP9 expression. It is well known that plaques that are prone to rupture contain large numbers of inflammatory and apoptotic cells, and these regions secrete large amount of MMP9.

Molecular Imaging Probes for Detecting Atherosclerotic Plaque

This molecular imaging study is aimed at detecting the pathobiological processes that occur in the atherosclerotic plaque. Obviously, the choice of imaging probe/s selected for imaging is critical. The ideal probe should target proteins expressed in the atherosclerotic plaque specifically and extensively, and it should have a high binding affinity and a high sensitivity and selectivity to target/s in the atherosclerotic plaque.

Based on these criteria, various investigators have targeted different proteins and components of plaque to image atherosclerotic plaque in vivo. Apoptosis resulting in a loss of cell density in the plaque is an important component of atherosclerosis, although its precise significance and the timing of its appearance in the atherosclerotic region remains a subject of conjecture. It is now well recognized that atherosclerotic lesions contain a large number of monocytes/macrophages as part of the inflammatory process, and the number of inflammatory cells predict vulnerability of plaque to rupture (Newby A C. *Arterioscler Thromb Vasc Biol*. 2008; 28:2108-14).

The rationale for targeting LOX-1 is that this molecule is highly expressed in advanced atherosclerotic plaque and activated endothelial cells, macrophages, platelets and dendritic cells. Besides being highly expressed, its activation leads to apoptosis, free radical generation, inflammatory cell recruitment, and expression of MMPs and tissue factor. Therefore, LOX-1 as a molecular imaging target may represent the full spectrum of pathological processes in atherosclerotic plaque. A recent study used $^{99m}$Tc-LOX-1 antibody to detect atherosclerotic plaque in a rabbit model (Ishino et al. J Nucl Med. 2008; 49:1677-85). However, use of this imaging probe was limited by low spatial resolution and poor signal to noise ratio because the half life of $^{99m}$Tc is about 6 hours and an antibody usually takes longer than 6 hours to bind to an antigen in vivo.

As disclosed herein, imaging probes were constructed using liposome as vectors to carry the LOX-1 antibody, fluorescent marker DiI, and $^{111}$In or Gd. The size of the liposome was kept less than 100 nm so that the liposomes could leave the vasculature, enter interstitial space and bind to the appropriate components of the atherosclerotic plaque. The liposome-LOX-1 antibody highly and specifically bound to the LOX-1 antigen, whereas, very little liposome-nIgG bound to the LOX-1 antigen. Notably, LOX-1 probes cleared slowly compared to nIgG probes in the Apo $E^{-/-}$ mice initially. The slower clearance might be related to the binding of the LOX-1 probe to LOX-1 antigen in the atherosclerotic plaque as well as to soluble LOX-1 fragments in the plasma; however, both probes were equally and rapidly cleared in the C57BL/6 mice. The slow clearance of LOX-1 probe in the Apo $E^{-/-}$ mice may allow greater binding of LOX-1 antibody to LOX-1 antigen and its uptake within the plaque. The half life of $^{111}$In is 2.8 days. The majority of LOX-1 probes were cleared in blood pool at 24 hours after injection. These features of the LOX-1 probe provided the rationale for imaging at 24 hrs after injection. As expected, a significant amount of liposome probes accumulated in the liver and spleen. However, this did not affect image quality since the scan was conducted from the aortic root to arch.

LOX-1 Imaging Signal and Vulnerability of Atherosclerotic Plaque to Rupture

Over the last decade, it has become evident that rupture-prone atherosclerotic plaques are seen in a majority of patients with life-threatening coronary syndromes. As mentioned earlier, these rupture-prone plaques are generally rich in inflammatory cells, exhibit few smooth muscle cells but large number of apoptotic cells, and release of locally generated MMPs. It is widely appreciated that the shoulder region of plaque is a common site in plaque rupture because it has more inflammation, apoptosis, shear stress and gene expression.

The LOX-1 probe was found to localize primarily in the shoulder region of plaques in the atherosclerotic $LDLR^{-/-}$ mice. This finding correlated with the distribution of LOX-1 expression seen by immunostaining of the plaque. Importantly, the LOX-1 probe was co-localized with macrophages, apoptotic cells and MMP9 expressing cells. A recent study in an atherosclerotic rabbit model found that $^{99m}$Tc-LOX-1 antibody accumulated selectively in atheromatous lesions which contain large numbers of macrophages and extracellular lipid deposits but fewer smooth muscle cells and collagen fibers. The results reported herein are particularly important since we showed co-localization of the LOX-1 probe to rupture-prone atherosclerotic regions in the murine models; these models are likely to be used more often than large animal models as molecular targeted approaches are generally devised in small animals.

Molecular Imaging Targeted to LOX-1 for Detecting Atherosclerotic Plaque

Molecular imaging using SPECT or PET fused with CT imaging has the potential to characterize the activity of atherosclerotic plaque. This approach has a high sensitivity, but the spatial resolution is low because of a suboptimal plaque-to-blood ratio and inadequate resolution of nuclear medicine imaging techniques in the mouse models. Molecular imaging using MRI provides clear information on the anatomy, function and spatial resolution, but the sensitivity is not as high as for SPECT or PET. No single imaging modality allows overall structural, functional, and molecular information as each imaging modality has its own strengths and weaknesses.

The combination of two imaging modalities might offer the prospect of improved diagnostic and therapeutic monitoring abilities. The LOX-1 imaging probe in this study was designed for SPECT and MRI. Multi-modality molecular imaging techniques can provide complementary information to define the characteristics of atherosclerotic plaque. As disclosed herein, we found that SPECT/CT clearly showed hotspots in the atherosclerotic region of aortic arch in Apo E–/– mice injected with LOX-1 probe, but not the nIgG probe. The data from MRI also demonstrated that there was strong post-Gd enhancement in atherosclerotic plaques from the aortic root to the arch in the LDLR–/– mice injected with LOX-1 probe. Again, there was no post-Gd enhancement in the LDLR–/– mice injected with nIgG probe. The specificity of LOX-1 imaging signal was further delineated by using LDLR–/– mice with LOX-1 abrogation. Previous studies have shown a marked reduction in atherogenesis in these double knockout mice. Consistent with these studies, we found a marked reduction in LOX-1 probe binding in the plaque and post-Gd enhancement in these double knockout mice in the present study.

These data from two different mouse models and two different imaging modalities adequately validate that LOX-1 can be used as a target for molecular imaging to detect atherosclerotic plaques.

In summary, we show that LOX-1 can be used as a molecular imaging target with high binding affinity, high sensitivity and selectivity in atherosclerotic plaques. LOX-1 targeting provides important information pertaining to the vulnerability of atherosclerotic plaques. These multimodality molecular imaging techniques are anticipated to have utility as clinically relevant non-invasive tools for detecting and monitoring rupture-prone plaques. These techniques may also be used to assess the efficacy of novel treatments that induce plaque regression and stabilization.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

The invention claimed is:

1. A LOX-1 imaging composition, said LOX-1 imaging composition comprises
   a plurality of liposome having a mean diameter of less than 100 nm, said liposomes comprising 1,2-Dioleoyl-sn-Glycero-3-Phosphocholine, cholesterol, N-hydroxysuccinimide ester of carboxy-PEG3400-DSPE-LOX-1 antibody, and at least one additional polymer selected from the group consisting of 1,1'dioctadecyl-3,3,3',3'-tetramethylindocarbocyanine perchlorate, diethylenetriaminepentaacetic acid α,ω-bis(8-stearoylamido-3, 6-diaoxaoctylamide) gadolinium complex and DTPA-phosphatidylethanolamine-SPECT contrast agent; and a pharmaceutically acceptable carrier.

2. The composition of claim 1 wherein the SPECT contrast agent is $^{111}$In.

* * * * *